United States Patent
Ziv et al.

(10) Patent No.: US 10,039,666 B2
(45) Date of Patent: Aug. 7, 2018

(54) APPARATUSES AND METHODS OF INTRAVAGINAL SUPPORT AND/OR DISTENSION

(75) Inventors: Elan Ziv, Ramat-Gan (IL); Amir Perle, Haifa (IL)

(73) Assignee: ConTIPI Medical Ltd., Caesarea (IL)

(*) Notice: Subject to any disclaimer, the term of this patent is extended or adjusted under 35 U.S.C. 154(b) by 640 days.

(21) Appl. No.: 13/879,401

(22) PCT Filed: Oct. 9, 2011

(86) PCT No.: PCT/IL2011/000796
§ 371 (c)(1),
(2), (4) Date: Apr. 14, 2013

(87) PCT Pub. No.: WO2012/049676
PCT Pub. Date: Apr. 19, 2012

(65) Prior Publication Data
US 2013/0192606 A1   Aug. 1, 2013

Related U.S. Application Data

(60) Provisional application No. 61/392,540, filed on Oct. 13, 2010.

(51) Int. Cl.
*A61F 6/08* (2006.01)
*A61M 31/00* (2006.01)
(Continued)

(52) U.S. Cl.
CPC ............ *A61F 6/08* (2013.01); *A61B 17/43* (2013.01); *A61F 2/005* (2013.01); *A61M 31/002* (2013.01); *A61F 2250/0067* (2013.01)

(58) Field of Classification Search
CPC .... A61F 6/08; A61F 2/005; A61F 6/16; A61F 2/0013; A61F 2/0027; A61F 6/06;
(Continued)

(56) References Cited

U.S. PATENT DOCUMENTS

5,014,722 A * 5/1991 Bauer ............... A61F 6/18
128/830
5,224,494 A * 7/1993 Enhorning ............... A61F 6/08
128/834
(Continued)

FOREIGN PATENT DOCUMENTS

DE        19816349 A1 * 10/1999 ............ A61F 2/005
WO    WO 2008/152628        0/2008
(Continued)

OTHER PUBLICATIONS

International Preliminary Report on Patentability dated Apr. 25, 2013 From the International Bureau of WIPO Re. Application No. PCT/IL2011/000796.
(Continued)

*Primary Examiner* — Victoria J Hicks
*Assistant Examiner* — Michelle J Lee

(57) ABSTRACT

An intravaginal support apparatus. The intravaginal support apparatus comprises a pessary ring having a substantially annular configuration and a narrowed configuration, a locking mechanism which retains and switches between the annular configuration and the narrowed configuration, and one or more expandable elements having expanded and unexpanded configurations, attached to one or more of the locking mechanism and the pessary ring. The pessary ring laterally expands from the narrowed configuration to the annular configuration; the expandable element expands outwardly of the pessary ring, from the unexpanded configuration to the expanded configuration.

17 Claims, 15 Drawing Sheets

(51) Int. Cl.
  *A61B 17/43* (2006.01)
  *A61F 2/00* (2006.01)
(58) Field of Classification Search
  CPC .... A61F 6/12; A61F 6/146; A61F 6/14; A61F 6/20; A61F 2/0022; A61F 2/0004; A61F 2250/0003; A61F 2250/001; A61F 2250/0039; A61F 2250/0065; A61F 2250/0071; A61F 2250/009; A61F 6/00; A61F 6/142; A61F 2/0009; A61B 17/12022–17/12045; A61B 17/06109; A61B 17/06066; A61B 17/12131; A61B 17/12136; A61B 17/1214; A61B 17/12145; A61B 17/12154; A61B 2017/00805
  USPC ............... 600/29, 31; 128/834, 836, 837
  See application file for complete search history.

(56) References Cited

U.S. PATENT DOCUMENTS

| | | | | |
|---|---|---|---|---|
| 5,603,685 | A * | 2/1997 | Tutrone, Jr. ............ | A61F 2/005 128/836 |
| 2003/0176761 | A1 * | 9/2003 | Brady .................... | A61F 2/00 600/29 |
| 2007/0089750 | A1 * | 4/2007 | Astani ................... | A61F 2/0045 128/830 |
| 2007/0203429 | A1 * | 8/2007 | Ziv ....................... | A61F 2/005 600/573 |
| 2009/0326573 | A1 * | 12/2009 | Miller ................... | 606/193 |
| 2010/0121270 | A1 * | 5/2010 | Gunday ............. | A61B 17/22012 604/98.01 |

FOREIGN PATENT DOCUMENTS

| | | |
|---|---|---|
| WO | WO 96/01084 | 1/1996 |
| WO | WO 2007/049154 | 5/2007 |
| WO | WO 2009/130702 | 10/2009 |
| WO | WO 2012/049676 | 4/2012 |

OTHER PUBLICATIONS

Communication Relating to the Results of the Partial International Search dated Feb. 9, 2012 From the Interantional Searching Authority Re. Application No. PCT/IL2011/000796.
International Search Report and the Written Opinion dated Aug. 28, 2012 From the International Searching Authority Re. Application No. PCT/IL2011/000796.
Communication Under Rule 164(2)(a) EPC dated Jun. 15, 2015 From the European Patent Office Re. Application No. 11788233.2.
Communication Pursuant to Article 94(3) EPC dated Jan. 28, 2016 From the European Patent Office Re. Application No. 11788233.2.

* cited by examiner

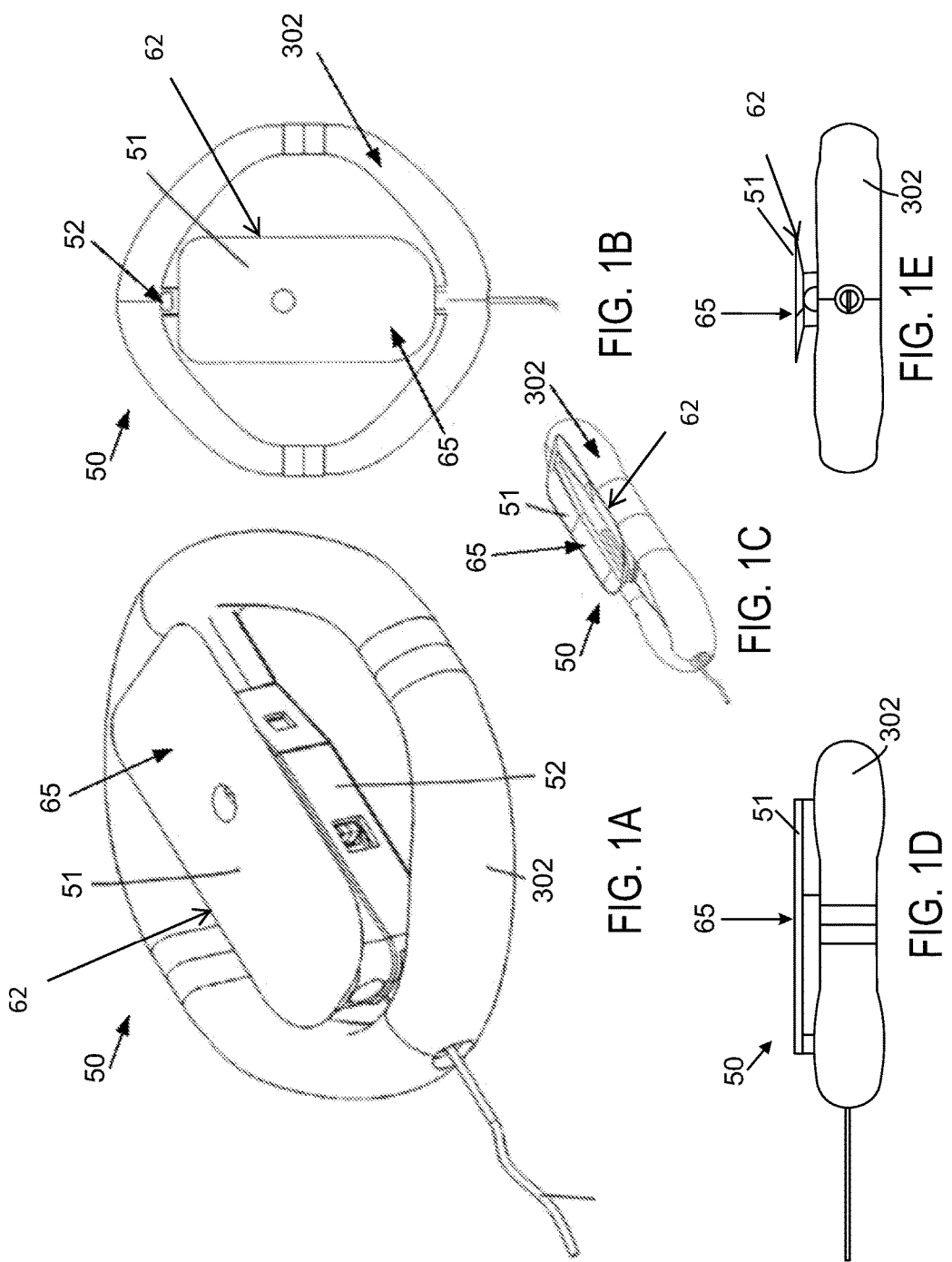

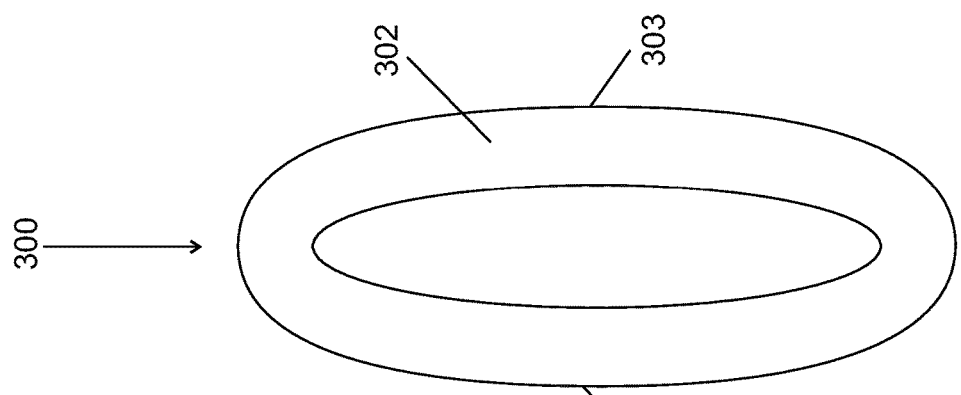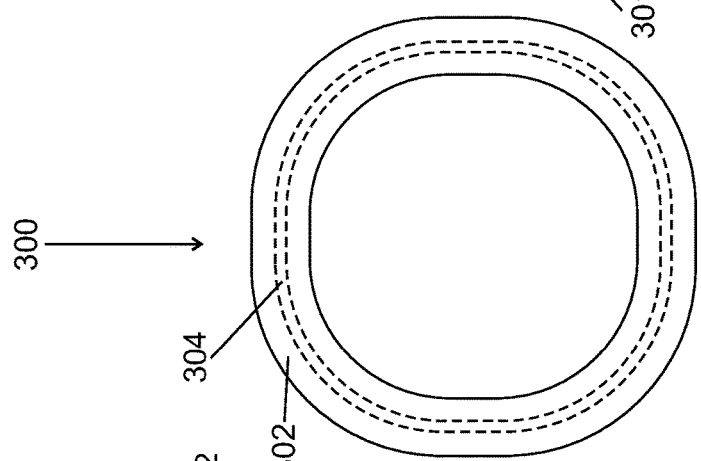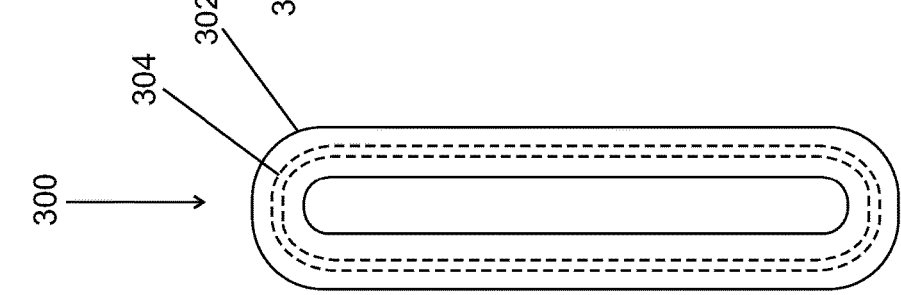

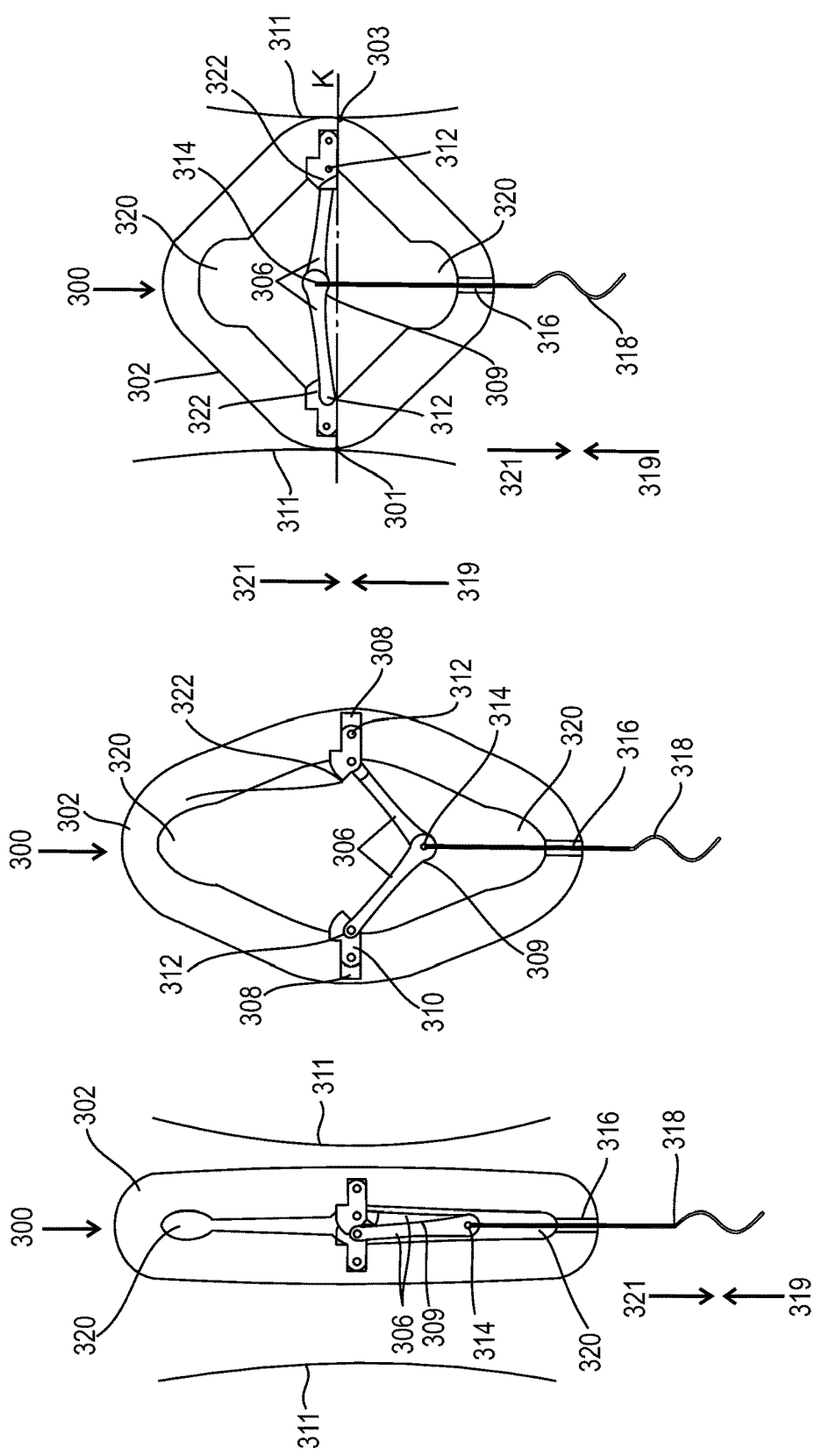

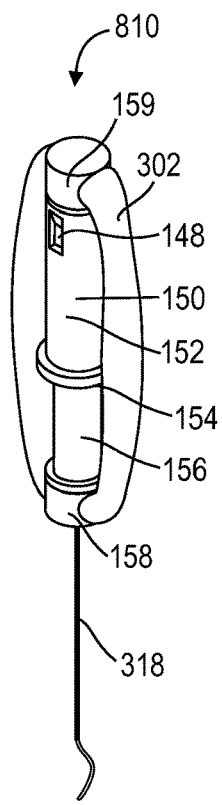 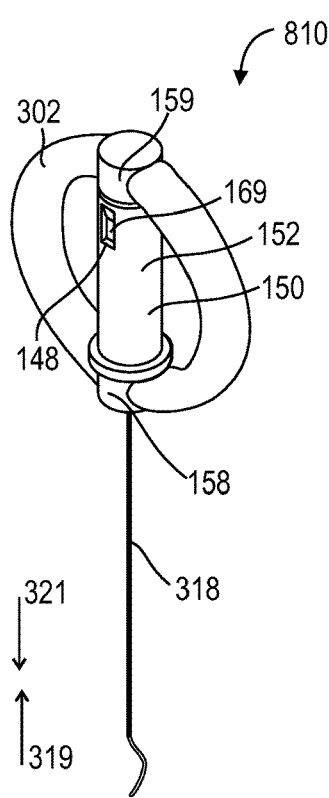 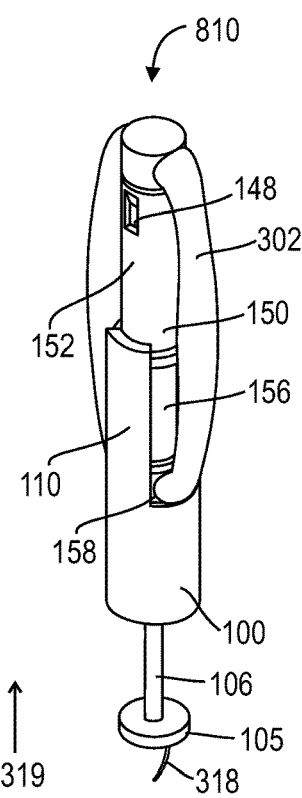
FIG. 5D   FIG. 5E   FIG. 5F
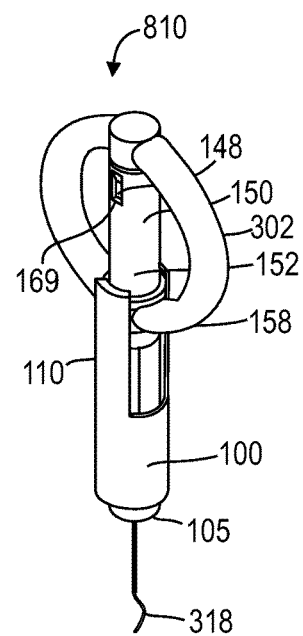
FIG. 5G

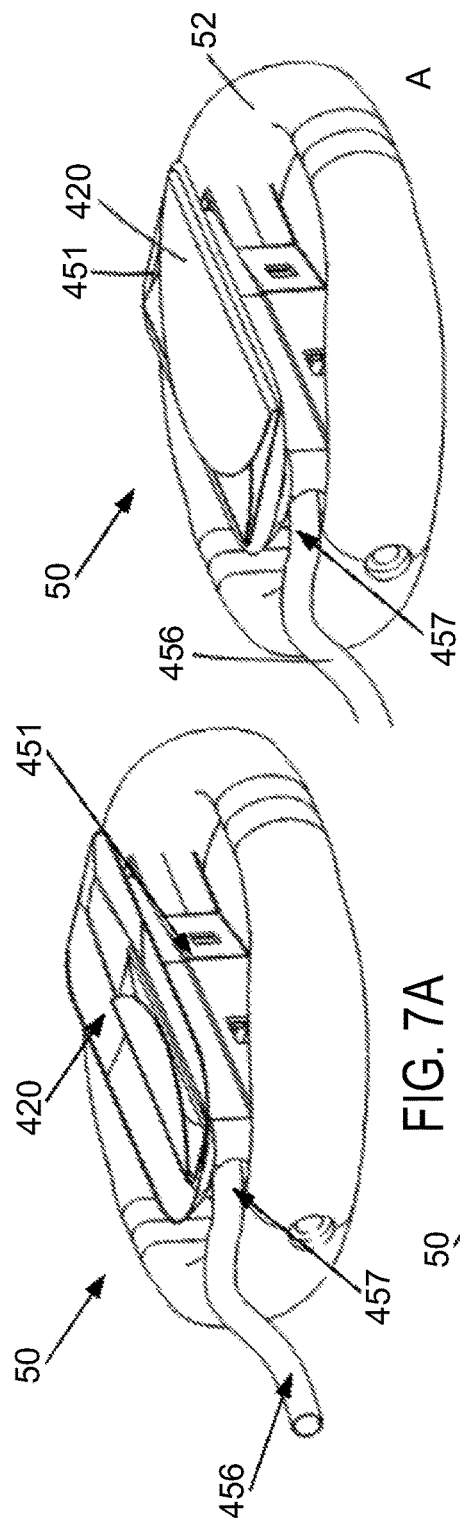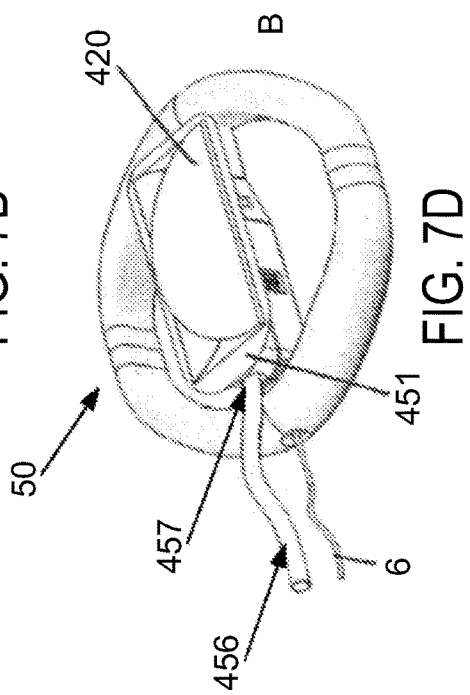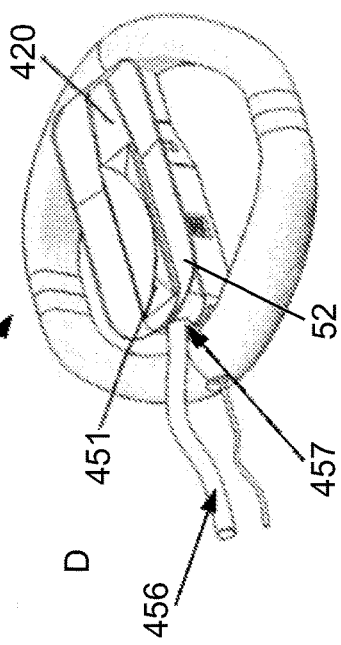

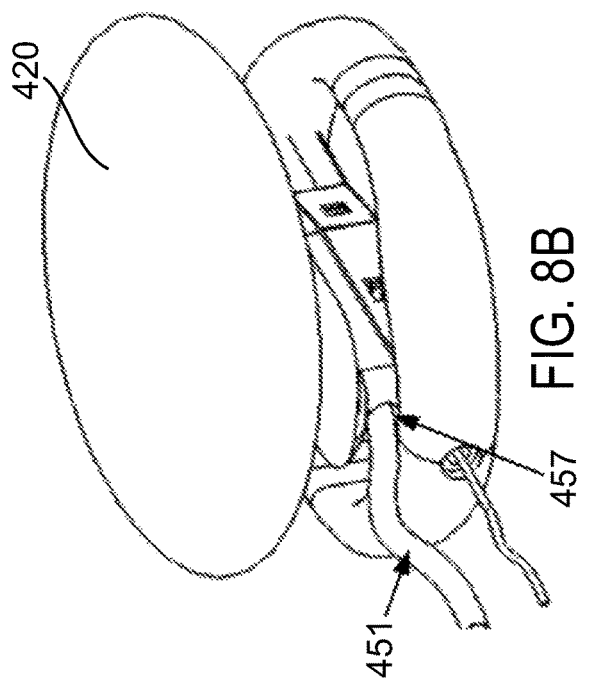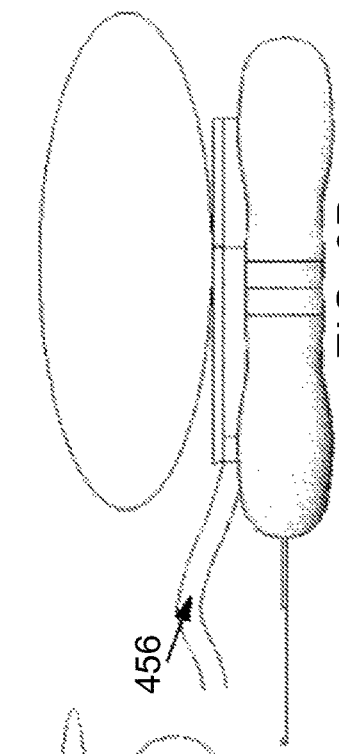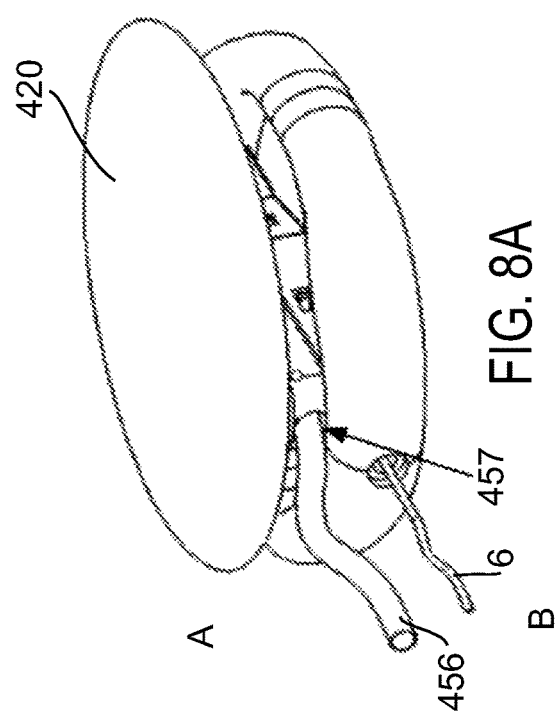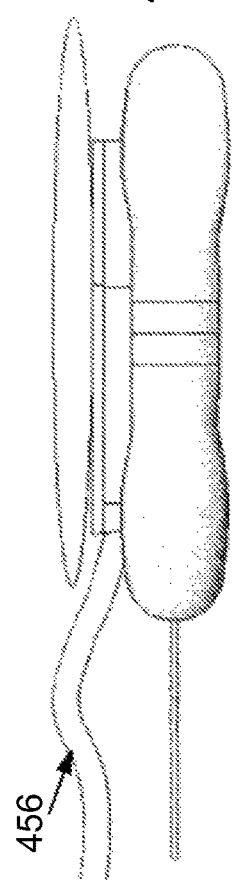

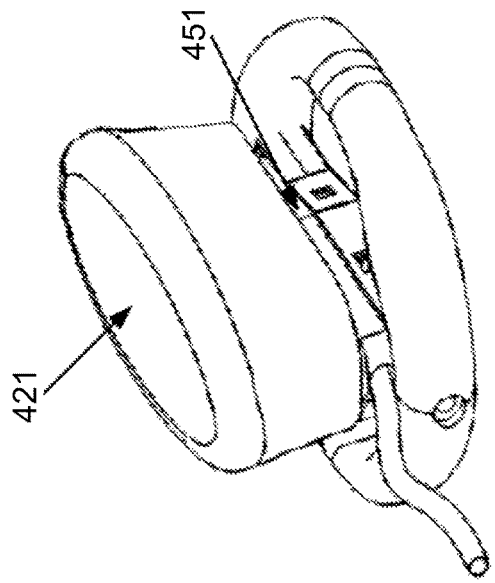
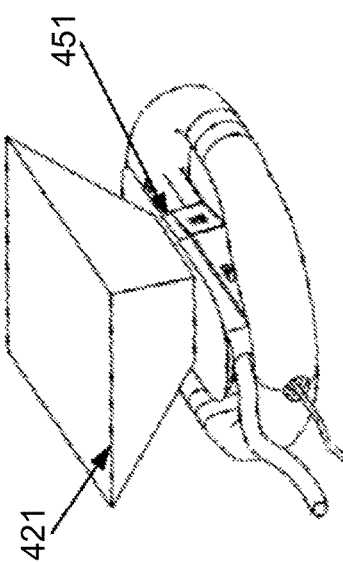
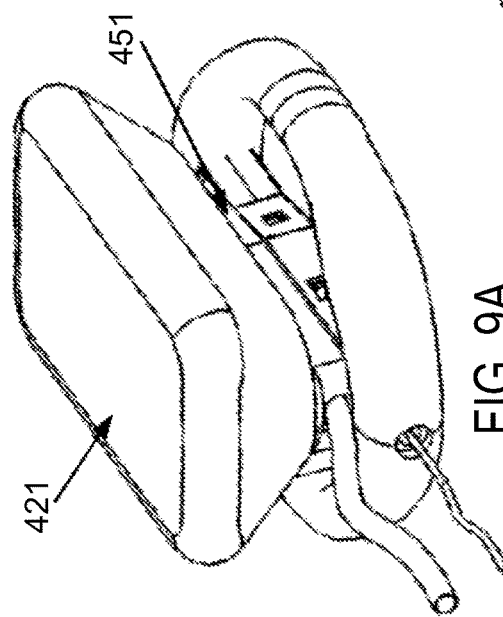
FIG. 9A
FIG. 9B
FIG. 9C

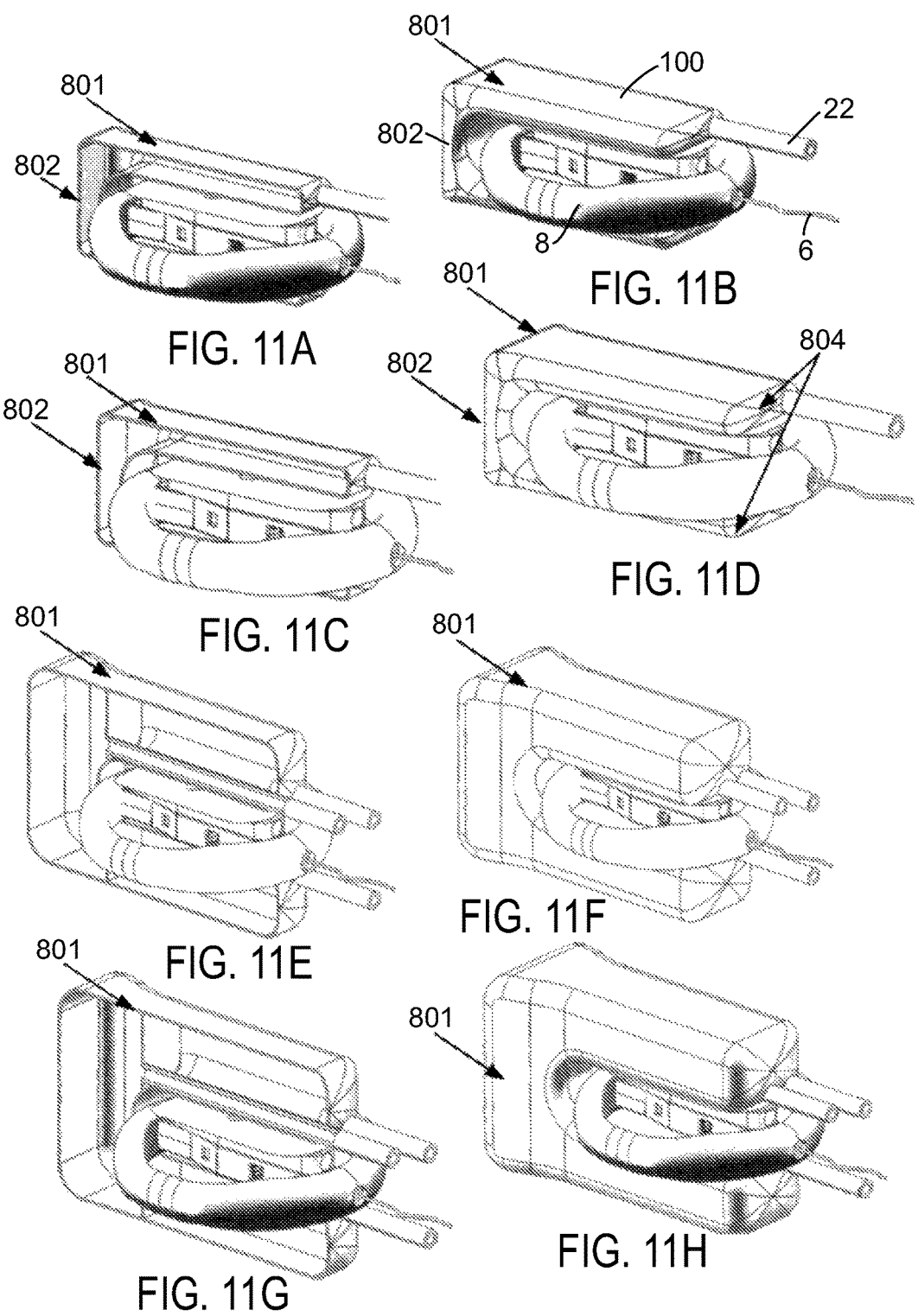

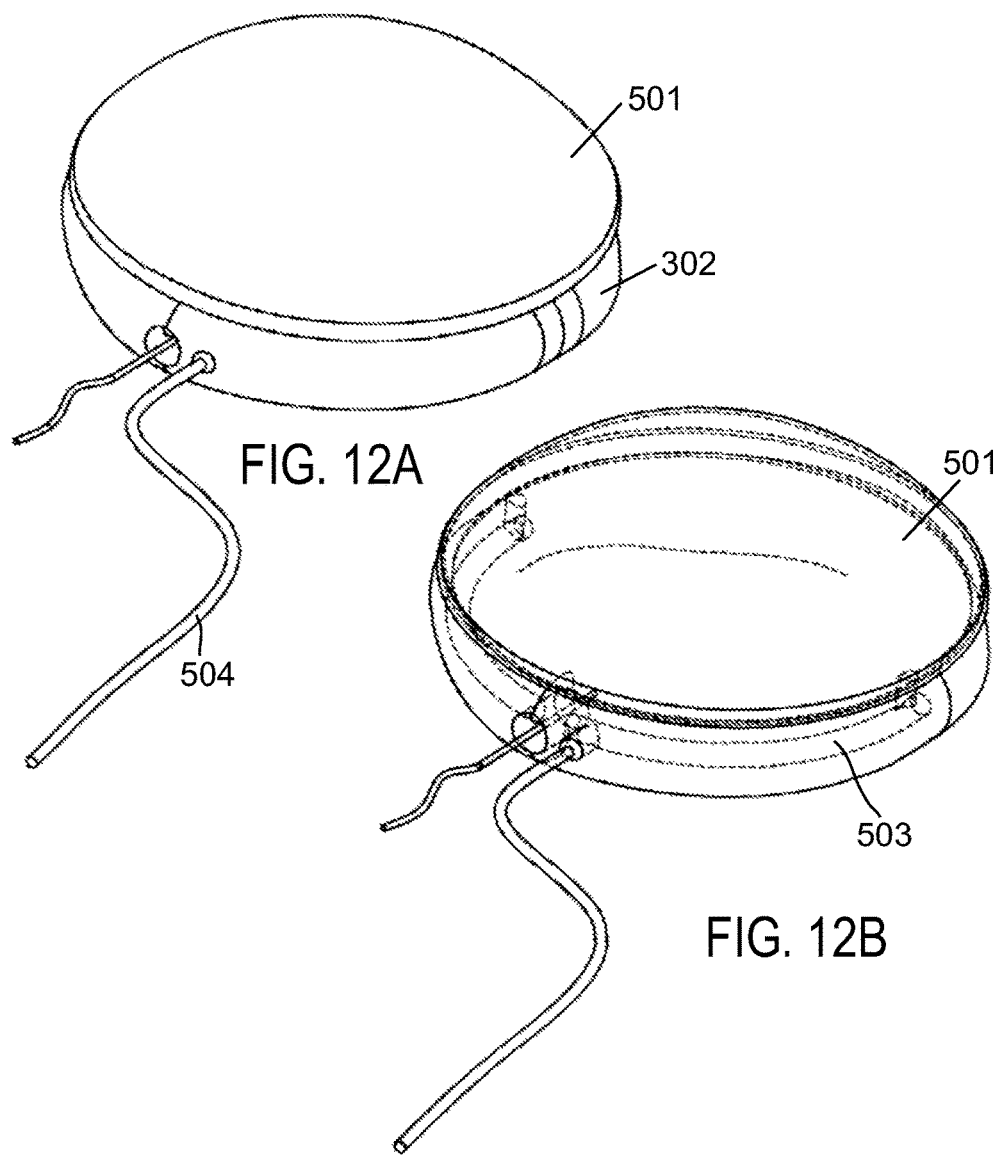
FIG. 12A
FIG. 12B
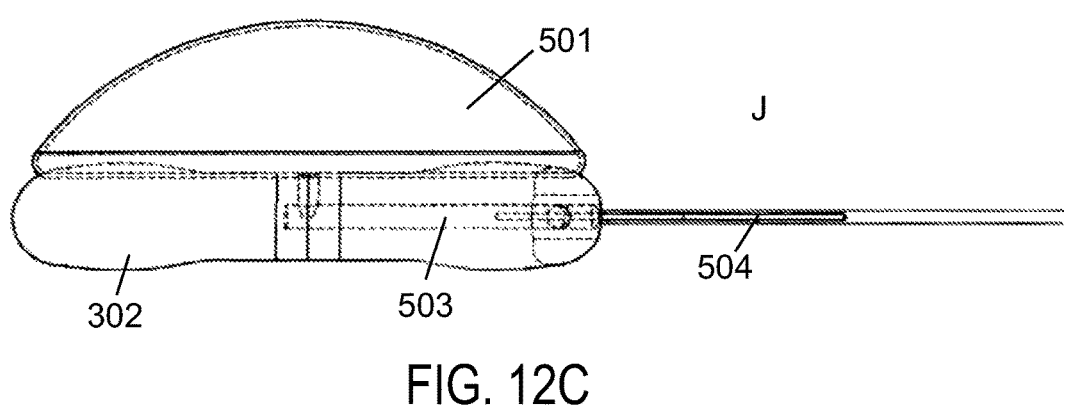
FIG. 12C

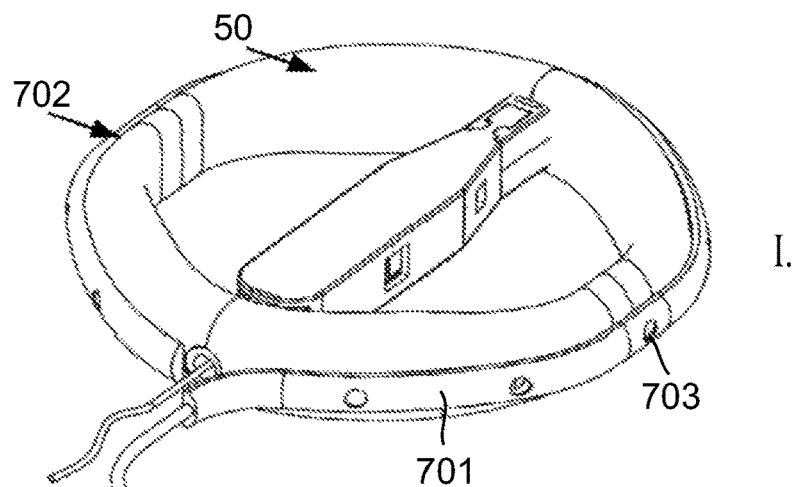
FIG. 13A
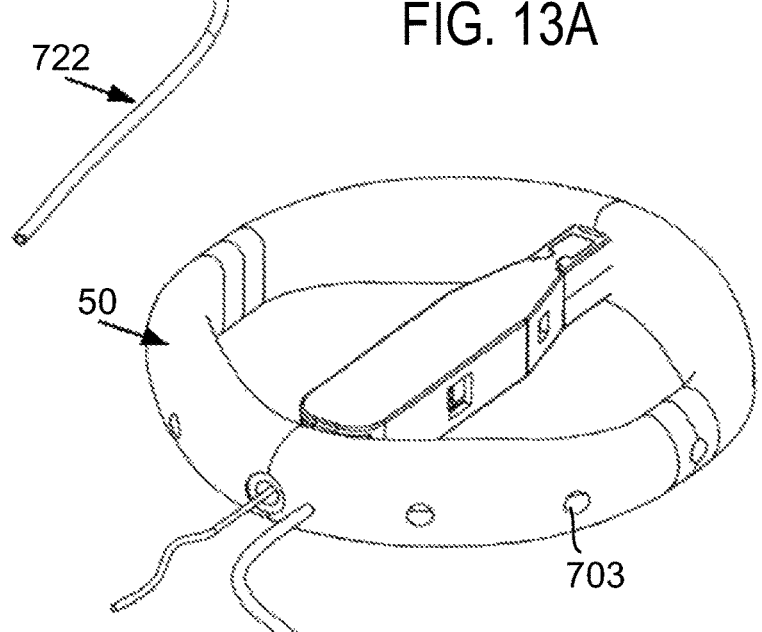
FIG. 13B
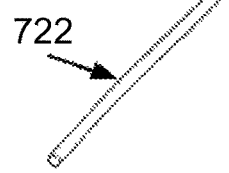

APPARATUSES AND METHODS OF INTRAVAGINAL SUPPORT AND/OR DISTENSION

RELATED APPLICATIONS

This application is a National Phase of PCT Patent Application No. PCT/IL2011/000796 having International filing date of Oct. 9, 2011, which claims the benefit of priority under 35 USC § 119(e) of US Provisional Patent Application No. 61/392,540 filed on Oct. 13 2010. PCT Patent Application No. PCT/IL2011/000796 incorporates by reference International Patent Application Publications Nos. WO2009/130702, WO2009/109966, WO2008/152628 and WO2005/087153. The contents of the above applications are all incorporated herein by reference as if fully set forth in their entirety.

FIELD AND BACKGROUND OF THE INVENTION

The present invention, in some embodiments thereof, relates to devices and methods for intravaginal treating and diagnosis and, more particularly but not exclusively, to devices and methods for drug delivery, vaginal support and distension, and/or the positioning of intravaginal diagnosis devices.

During the last years various intra vaginal devices have been developed for treatment and diagnosis. Some of these devices are designed for treating pelvic organ prolapse (POP). POP occurs when the network of muscles, ligaments, and tissues that hold the pelvic organs in place is weakened and one or more pelvic organs move into the vaginal cavity. Pelvic organ prolapse occurs as a result of normal aging, childbirth, pelvic surgery or trauma. Symptoms of POP are very bothering; depending on the type of POP experienced. For example, cases of rectocele may result in difficulty and/or pain associated with defecating, which would not normally be present in cases of vaginal vault prolapse. General symptoms associated with most forms of POP include, but are not limited to, Bulging of a lump out of the vagina, Feeling of pelvic heaviness, Pelvic and/or lower back pain, Stress Incontinence, Dyspareunia (pain during sexual intercourse), Excessive vaginal discharge, Recurrent bladder infections, Voiding difficulties up to retention, Difficulty emptying the bowels, Urgency & Urge Incontinence, Sexual discomfort & inability to reach orgasm, etc.

To avoid surgical procedures to treat pelvic organ prolapse, a number of non-surgical vaginal devices, pessaries, have been designed to be inserted into the vagina by a surgeon, medical assistant or user.

For example, international patent application Pub. No. WO2009/130702 filed on Apr. 23, 2009, which is incorporated herein by reference, describes devices for supporting a prolapsed organ which comprise a ring-like body optionally having a naturally occurring substantially flat and substantially planar narrowed configuration, the ring-like body configured with a size suitable for insertion into a vagina and to be expanded by a support element such that in the expanded configuration an outer periphery of the ring-like body contacts a portion of the vagina and stretches at least a portion of a prolapsed vaginal wall, thereby substantially alleviating prolapse of at least one pelvic organ. This device may include a support element comprising two moveably connected arms configured to support the ring in the expanded configuration.

SUMMARY OF THE INVENTION

According to some embodiment of the present invention, there is provided an intravaginal support apparatus. The intravaginal support apparatus comprises a pessary ring having a substantially annular configuration and a narrowed configuration, a locking mechanism which retains and switches between the annular configuration and the narrowed configuration, and at least one expandable element having expanded and unexpanded configurations, attached to at least one of the locking mechanism and the pessary ring. The pessary ring laterally expands from the narrowed configuration to the annular configuration, the at least one expandable element expanding outwardly of the pessary ring, from the unexpanded configuration to the expanded configuration.

Optionally, the at least one expandable element are attached on top of the pessary ring.

Optionally, the at least one expandable element expands at least one of upwardly of the pessary ring, in front of the pessary ring, forming an apical extension, and downwardly of the pessary ring.

Optionally, the at least one expandable element comprises at least one balloon and at least one conduit for inflating the at least one balloon to switch between the unexpanded configuration and the expanded configuration.

More optionally, the at least one balloon is annularly attached to the surface of the pessary ring, the at least one conduit being at least partly mounted within the pessary ring or along the pessary ring.

More optionally, the at least one balloon comprises a plurality of balloons attached to opposing sides of the intravaginal support apparatus.

More optionally, intravaginal support apparatus further comprises a pressure gauge for measuring the pressure within the at least one balloon.

More optionally, intravaginal support apparatus further comprises a pump for delivering fluids into the balloon according to the pump.

More optionally, intravaginal support apparatus further comprises a pump which delivers fluids into the balloon and a controller which controls the pump according to a selected pressure control plan.

Optionally, the at least one expandable element comprises a U-shaped balloon placed to expand outwardly above, below, and in front of the pessary ring.

More optionally, the U-shaped balloon having a plurality of compartment, each set to be inflated by applying a different pressure.

More optionally, the at least one balloon comprises a balloon having a shape selected from a group consisting of: an oval shape, a box shape, and a pyramid shape.

Optionally, the intravaginal support apparatus further comprises a carrier for detachably attaching the at least one expandable element to the locking mechanism.

Optionally, the at least one expandable element comprises a plurality of balloon and at least one conduit for inflating each the balloon to in a different inflating rate.

According to some embodiment of the present invention, there is provided a method for providing intravaginal support using an intravaginal support apparatus having a pessary ring having narrowed and substantially annular configurations and at least one expandable element into an intravaginal lumen. The method comprises inserting the intravaginal support apparatus with the pessary ring in the narrowed configuration into an intravaginal lumen, laterally expanding the pessary ring by inducing a switch between the narrowed configuration to the substantially annular configuration in the intravaginal lumen, and at least one of downwardly expanding and upwardly expanding the at least one expandable element in the intravaginal lumen.

Optionally, the method is performed after a vaginal operation so as to apply pressure on inner walls of the intravaginal lumen.

Optionally, the at least one of downwardly expanding and upwardly expanding is performed to provide vaginal packing after the forming of intravaginal sutures in inner walls of the intravaginal lumen.

Optionally, the at least one of downwardly expanding and upwardly expanding is performed by expanding the at least one expandable element to apply a selected pressure on inner walls of the intravaginal lumen.

Optionally, the at least one of downwardly expanding and upwardly expanding is performed by injecting fluids into the at least one expandable element.

Optionally, the at least one expandable element remain in the intravaginal lumen for a period of at least 24 hours.

More optionally, the at least one expandable element comprises at least one balloon, further comprises intermittently adjusting a pressure within the at least one balloon during the period.

More optionally, the at least one expandable element is maintained in an expanded state for a period of at least 24 hours.

More optionally, the at least one expandable element is maintained in an expanded state for at least one of widening and elongate the intravaginal lumen while maintaining the flexibility of the intravaginal walls.

Optionally, the method further comprises implanting an intravaginal gauze in proximity to suture lines in the intravaginal lumen before the inserting and extracting the intravaginal gauze from the intravaginal lumen before the inserting; wherein the at least one of downwardly expanding and upwardly expanding is performed to apply pressure on the suture lines.

According to some embodiment of the present invention, there is provided an intravaginal support apparatus that comprises a pessary ring having a substantially annular configuration and a narrowed configuration, a locking mechanism which retains and switches between the annular configuration and the narrowed configuration, and an irrigation unit attached to at least one of the locking mechanism and the pessary ring and having an inlet receive fluids from a fluid conduit and at least one outlet to irrigate an intravaginal walls with the fluids. The pessary ring laterally expands from the narrowed configuration to the annular configuration.

Optionally, the at least one outlet comprises a plurality of outlets, the plurality of outlets are annularly distributed along the pessary ring.

More optionally, the irrigation unit is set to continuously or intermittently apply flow of the fluids on vaginal walls in an intravaginal lumen during a period of at least few hours.

More optionally, the irrigation unit is set to perform drug elution via the at least one outlet.

According to some embodiment of the present invention, there is provided an intravaginal support apparatus that comprises a pessary ring having a substantially annular configuration and a narrowed configuration, a locking mechanism which retains and switches between the annular configuration and the narrowed configuration, and a carrier mounted on the locking mechanism an configured to support a member of a group consisting of an expandable element, a drug delivery element, an irrigation unit, an insemination unit, and an intra-vaginal irradiation source. The pessary ring laterally expands from the narrowed configuration to the annular configuration to facilitate anchoring the member in the intravaginal lumen for a period of at least one hour.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-1E, which are images of an exemplary intravaginal support apparatus having a support carrier for providing an intravaginal support to an intravaginal element, according to some embodiments of the present invention;

FIGS. 2A-2C are schematic illustrations of an exemplary pessary ring that may be used according to some embodiments of the present invention;

FIGS. 3A-3C depict an exemplary locking mechanism for supporting a pessary ring in the substantially annular and narrowed configurations;

FIGS. 5D-5G depict an applicator having a linear expansion mechanism for implanting a vaginal support apparatus, according to some embodiments of the present invention;

FIGS. 7A-7D are schematic illustrations which depict a vaginal support apparatus having a carrier that supports a folded inflatable balloon, according to some embodiments of the present invention;

FIGS. 8A-8D are schematic illustrations which depict the vaginal support apparatus depicted in FIGS. 7A-7D with the folded inflatable balloon in an inflated state, according to some embodiments of the present invention;

FIGS. 9A-9C are schematic illustrations which depict a vaginal support apparatus supporting balloons having different exemplary shapes, according to some embodiments of the present invention;

FIGS. 11A-11H are schematic illustrations which depict a vaginal support apparatus having a carrier which supports a U-shaped balloon which covers portions of the top and bottom sides of the vaginal support apparatus, according to some embodiments of the present invention;

FIGS. 12A-12C are schematic illustrations which depict a vaginal support apparatus having a pessary ring that supports the radial edges of a round balloon, according to some embodiments of the present invention;

FIGS. 13A-13B which depict the intravaginal support apparatus having an annular irrigation unit mounted thereon, according to some embodiments of the present invention.

DESCRIPTION OF EMBODIMENTS OF THE INVENTION

Figure 4:
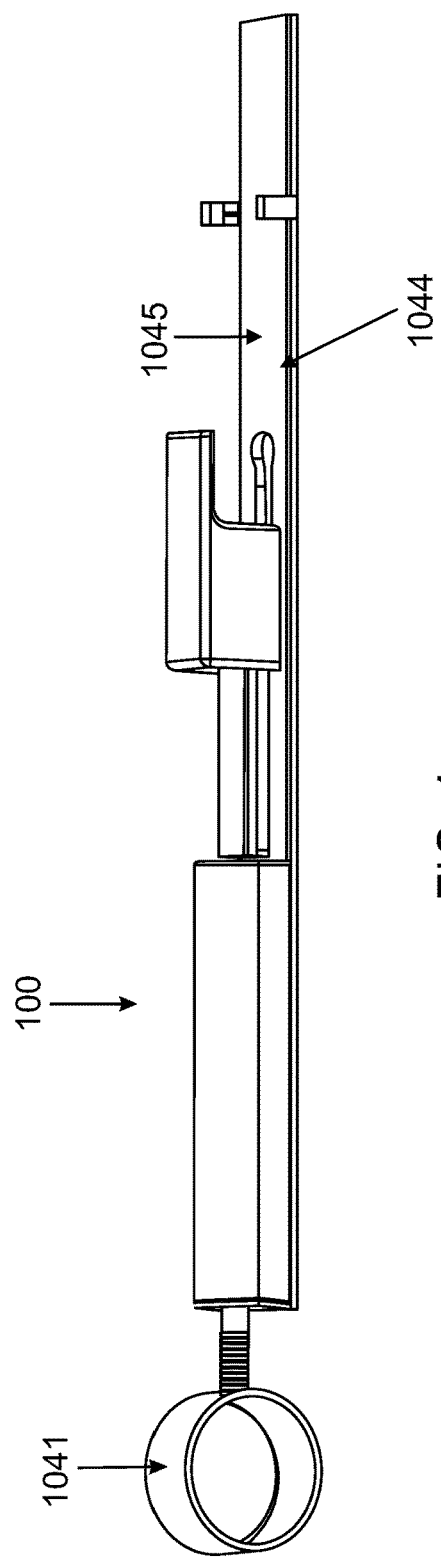
FIG. 4 and/or FIGS. 5A-5C depict applicators of implanting vaginal support apparatuses, such as depicted in FIGS. 1A-1E, according to some embodiments of the present invention.

The present invention, in some embodiments thereof, relates to devices and methods for intravaginal treating and diagnosis and, more particularly but not exclusively, to devices and methods for drug delivery, vaginal support, and/or the positioning of intravaginal diagnosis devices.

According to some embodiments of the present invention, there is provided an intravaginal support apparatus having a pessary ring for anchoring it in the intravaginal lumen and one or more expandable element which are set to expand in the vaginal lumen, providing an intravaginal support, bleeding control, postoperative treatment and the like. The intravaginal support apparatus includes a pessary ring that has a substantially annular configuration for supporting the device in one place and a narrowed configuration for facilitating the insertion thereof into the vagina. The intravaginal support apparatus further includes a locking mechanism which retains and switches between the annular and narrowed configurations and one or more expandable elements, such as balloon, which have expanded and unexpanded configurations (for example inflated and folded configurations), attached to the locking mechanism and/or to the pessary ring, for example as described below. The pessary ring laterally expands from the narrowed configuration to the annular configuration and the expandable elements expand upwardly and/or downwardly from the unexpanded configuration to the expanded configuration. The expandable elements, for example the balloons, may have various sizes and shapes, for example a box shape, a pyramid shape, an oval shape, a U-shape and the like.

According to some embodiments of the present invention, there is provided an intravaginal support apparatus which comprises the pessary and the locking mechanism which are outlined above and described below and an irrigation unit attached to the locking mechanism and/or the pessary ring and having an inlet receive fluids such as disinfectants, medicaments and/or diagnostic agents, from a fluid conduit and one or more outlets to irrigate an intravaginal walls with the fluids. According to some embodiments of the present invention, there is provided a method for providing intravaginal support using an intravaginal support apparatus, such as the aforementioned intravaginal support apparatus. The method is based on inserting the intravaginal support apparatus into an intravaginal lumen, laterally expanding the pessary ring by inducing a switch between the narrowed configuration and the substantially annular configuration in the intravaginal lumen, downwardly and/or upwardly expanding the expandable elements in the intravaginal lumen to provide intravaginal support, treatment and/or bleeding control.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Reference is now made to FIGS. 1A-1E, which are images of an exemplary intravaginal support apparatus 50 having a support carrier 51 for providing an intravaginal support to an intravaginal element, according to some embodiments of the present invention. The intravaginal element may be a drug delivery device and/or an intravaginal vaginal support device for pelvic support disorders such as pelvic organ prolapse (POP), urinary incontinence (UI), and anal incontinence (AI). The intravaginal support apparatus 50 includes a locking mechanism 52 having a narrowed configuration for facilitating the vaginal penetration of the intravaginal support apparatus 50 and a substantially annular configuration for applying pressure on opposite vaginal walls and/or expanding so as to be mounted in a fixed location in the vaginal lumen. Optionally, the intravaginal support apparatus 50 includes a pessary ring 302 that is connected to a locking mechanism 52. The locking mechanism 52 holds the pessary ring 302 in the substantially annular and narrowed configurations. For example, FIGS. 2A-2C, are schematic illustrations of an exemplary pessary ring 51 that may be used according to some embodiments of the present invention. FIG. 2A depicts a pessary ring 302 having a rhomboid narrowed configuration for insertion into the vaginal lumen. As shown in FIG. 2B, the pessary ring 302 expands to press the vaginal walls and thereby substantially alleviates pelvic organ prolapse. In some embodiments of the invention, in the narrowed configuration, the pessary ring 302 may have an oval shape, as shown in FIG. 2C, or a triangular shape (not shown). The various shapes for the pessary ring 302 in the narrowed configuration are determined by, for example, ease of insertion and/or the desired shape of the pessary ring 302 in the substantially annular configuration. It should be noted that FIGS. 2A-2C do not depict the carrier 52 depicted in FIGS. 1A-1C and described below.

FIGS. 3A-3C depict an exemplary locking mechanism 309 for retaining and switching between substantially annular and narrowed configurations of the pessary ring 302. Optionally, the locking mechanism 309 comprises two arms 306 that are rotatably connected at hinge 314, alternately referred to as rotation axis 314. Optionally a string ring 318 is attached to the rotatable connection that serves to unlock arms 306, for example as explained in international patent application Pub. No. WO2009/130702 filed on Apr. 23, 2009, which is incorporated herein by reference. Arms 306 are attached to limiters 310 along pessary ring 302 with peripheral hinges 312.

Initially, in the narrowed configuration, is inserted into a vagina 311 with arms 306 folded. During ring implant, hinge 314 is pressed in a direction 319 to cause pessary ring 302 to expand while arms 306 unfold (FIG. 3B). Pessary ring 302 achieves a substantially annular configuration (FIG. 3C) in which support curves 301 and 303 press laterally against the tissue of opposite and lateral aspects of vagina 311. In the substantially annular configuration, limiter edges 322 press against arms 306, and lock arms 306 to maintain locking mechanism 302 as a span across pessary ring 302 while forming an angle having an apex above a transverse line k-k. It should be noted that FIGS. 3A-3C do not depict the carrier 52 which is depicted in FIGS. 1A-1C and described below.

Figures 5A, 5B, 5C:
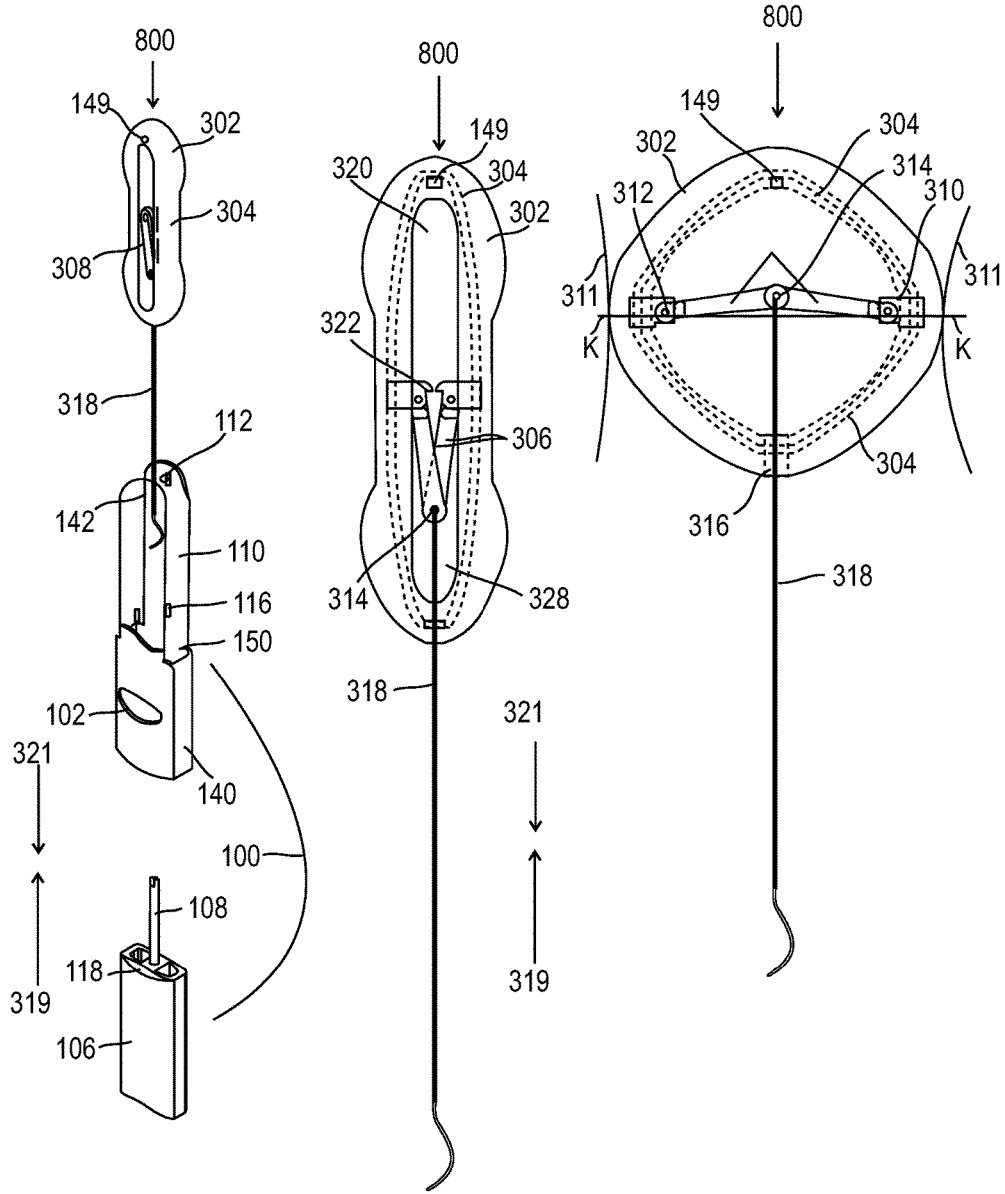

In use, the intravaginal support apparatus 50 is inserted into the vagina using an applicator 100, for example as shown by FIG. 4 and/or by FIGS. 5A-5C which a reference thereto is also made herein.

Optionally, the intravaginal support apparatus 50 includes a number of pessary ring 302 which are catenated one after the other. In such an embodiment each pessary ring 302 has a respective locking mechanism 302 and the locking mechanisms 302 are mechanically connected to one another, facilitating configuration switch of all the pessary rings, optionally simultaneously. Such a structure may require using pessary rings 302 with a limited diameter and facilitate the anchoring of slender tools to the carrier 51.

In FIG. 4, the applicator 100 has a handle 1041 connected to shaft 1042 that is set to be connected to the locking mechanism of the intravaginal support apparatus 50. The pulling and pushing of the handle 1041 switches between the narrowed configuration and the annular configuration, for example as described above. The applicator 100 has a backbone 1044 with an open receiving part 1045 for receiving the intravaginal support apparatus 50. The open receiving part 1045 has one surface for detachable attach the intravaginal support apparatus 50. In such a manner, the applicator 100 can detachable attach the intravaginal support apparatus 50, regardless to the size and/or shape of the carrier 51 and optionally allows expanding the one or more expandable elements before the intravaginal support apparatus 50 is implanted.

Referring now to FIG. 5A, where the applicator 100 includes a housing 140 which has an ovoid cross sectional profile along the transverse plane; a profile configured to match the user anatomy, as vagina 311 is parted during ring insertion of pessary assembly 800. As shown in FIG. 5A, housing 140 includes applicator arms 110 which include a first snap 142 and a second snap 112, respectively, which removably snap into receptacles 149 on either side of the upper portion of pessary ring 302, see United States Patent Application no. 2009/0266367, which is incorporated herein by reference.

It should be noted that FIGS. 5A-5C do not depict the carrier 52 that is depicted in FIGS. 1A-1C and described below.

In the narrowed configuration, pessary ring 302 is attached to applicator 100, as shown in FIG. 5A. The bottom portion of pessary ring 302 is set in housing 140, first snap 142 and second snap 112 snap into receptacles 149. To expand pessary ring 302, the first and third fingers are placed in convex recesses 102, on the front and back of housing 140, while the user's second finger pushes plunger 106 through housing 140 in direction 319. Movement of plunger 106 causes a hollow rod 108 to press arms 306 in direction 319, thereby extending arms 306 as shown in FIGS. 5D-5E. Arms 306 extend until pessary ring 302 attains the substantially annular shape shown in FIG. 5C and arms 306 form an angle having an apex above line K-K, as noted above. Following expansion of pessary ring 302, applicator arms 110 are pushed outwardly, as a result of movement of an upper slope 118 of plunger 106 over inner projections 116 on either side of applicator arms 110. As the upper slope 118 passes the inner projections 116, the walls of the housing 140 bulge outwardly, and the applicator arms 110 move apart, releasing the pessary ring 302. The applicator 100 is removed from pessary ring 302 and out of the vagina 311 leaving the pessary ring in the substantially annular configuration in the vagina 311 as shown in FIG. 5C. Removal of the pessary ring 302 from the vagina occurs when the string ring 318 is pulled in direction 319 so that arms 306 resume the position seen in FIG. 5B with the pessary ring 302 in the narrowed configuration.

According to some embodiments of the present invention, for example as depicted in FIGS. 5D-5G, the supporting mechanism has a linear expansion path, switching from increasing the distance between two opposing portions of the pessary ring 302, forming an oval shape, to reducing the distance between these portions to a diameter distance, increasing the circularity of the pessary ring 302. FIGS. 5D-5G show embodiments of a sliding pessary 810 having a smaller diameter tube 156 that slides into a larger diameter tube 152 along a linear expansion path. The larger diameter tube 152 is attached at an upper connector portion 159 on the pessary ring 302, and smaller diameter tube 156 is connected to a lower connector portion 158 on the pessary ring 302. As smaller diameter tube 156 slides into larger tube 152 in direction 321, pessary ring 302 is caused to expand (FIG. 5E). FIGS. 5F-5G show sliding pessary 810 assembled on the applicator 100 with the string ring 318 emerging from the hollow tube 106 that is connected the plunger handle 105. When the pessary ring 302 is in the elongated, narrowed configuration (FIG. 5F), the sliding pessary 810 is placed in the vagina. The plunger handle 105 is pressed in direction 319 so that the flat base presses against lower connector the portion 158, causing smaller the diameter tube 156 to telescope into the larger diameter tube 152, resulting in the above-noted expansion of pessary ring 302.

When the pessary ring 302 is in a substantially annular configuration it anchors the intravaginal support apparatus 50 within the intra vaginal lumen. As such, the anchoring of the intravaginal support apparatus 50 induces the anchoring of the one or more intravaginal devices which are supported by the carrier 51. Optionally, the carrier 51 includes a connecting element, such as one or more flanges, screws, clips, and/or fasteners which are used to dock the intravaginal devices to the intravaginal support apparatus 50. For example, an upper receiving recess for receiving a screw or a projection of a carried intravaginal device may be added to the carrier 51.

Figure 6A:
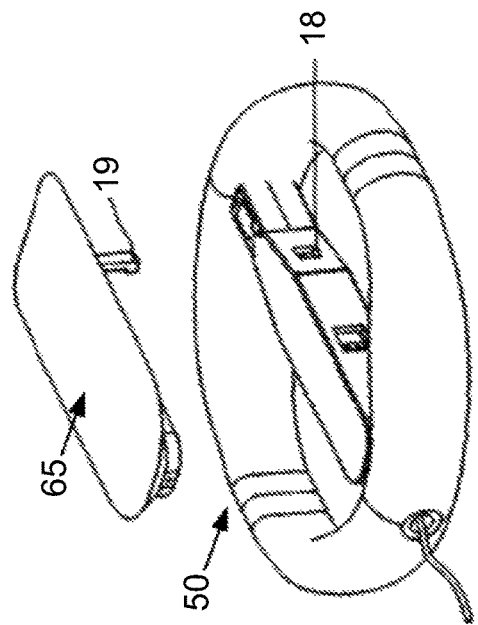
FIG. 6A-6C are schematic illustrations which depict a vaginal support apparatus having a carrier set on a locking mechanism and has one or more receiving recesses for receiving one or more projections 19 of the planer surface, according to some embodiments of the present invention.
Figure 6B:
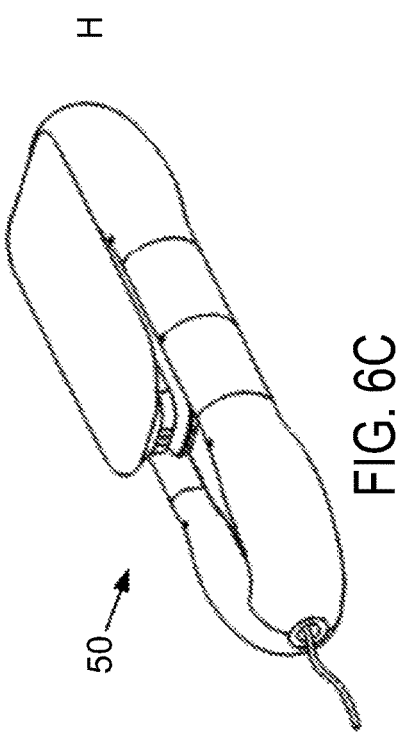
Figure 6C:
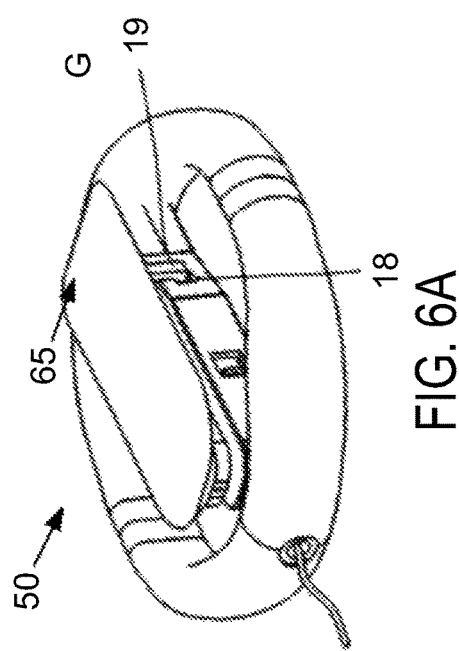

Optionally, as shown at FIGS. 1A-1C, the carrier 51 has a planar surface 65 connected to its top. The planar surface has a periphery lateral edge 62. Optionally, the carrier 51 is shaped according to the width of the intravaginal support apparatus 50 when the pessary ring 302 is in a narrowed configuration. Optionally, the periphery lateral edge 62 is slightly wider than the pessary ring 302 in a narrowed configuration. According to some embodiments of the present invention, the planar surface 65 is detachable. For example, as shown in FIG. 6A-6C, the carrier 51 is set on a locking mechanism 52 and has one or more receiving recesses 18 for receiving one or more projections 19 of the planar surface 65.

As shown at FIGS. 1A-1D, the intravaginal support apparatus 50 has a carrier 51. Such a carrier 51 may be connected to one or more expandable elements, such as wire mesh structures, balloons, and/or wire mesh structures covered with balloons, according to some embodiments of the present invention. For example, in FIGS. 7A-7D, a carrier 451 that is connected to the intravaginal support apparatus 50 supports a folded balloon 420 that is adhered or otherwise attached to the carrier 451, according to some embodiments of the present invention. The folding reduces the volume of the balloon facilities the insertion thereof, with the intravaginal support apparatus 50, into the vaginal lumen. Optionally, the carrier 451 is connected to an external conduit 456, such as a tube that allow conducting fluids, for example air, liquid, gel, and/or liquid-gel. Optionally, the carrier 451 has a lateral aperture 457 for connecting the external conduit 456 and a top output for filling an expandable element connected to the carrier 451, such as the folded balloon 420. Optionally, the carrier 451, the inner conduit, and the external conduit 456 are molded as a single unit. In the embodiment depicted in FIGS. 7A-7D, the external conduit 456 supplies fluids via the carrier 451 into the folded balloon 420. The flowing of the fluid expands the folded balloon 420, providing additional intravaginal support above the implanted pessary ring 302. FIGS. 8A-8D depict the intravaginal support apparatus 50 of FIGS. 7A-7D with the folded balloon 420 in an inflated state. The balloon 420, and any other balloon referred to herein may be a compliant balloon, a semi-compliant balloon or a noncompliant balloon made of biocompatible materials. The balloon 420, and any other balloon referred to herein may be covered with medicaments for direct delivery. In such a manner, medicaments may be applied directly on inner walls of the vagina, for example for treating sutures after an operations and/or for slow release of drug.

It should be noted that the folded balloon 420 may be designed to have any of various shapes. FIG. 8C depicts the intravaginal support apparatus 50 when it supports a balloon having a relatively flat oval shape in an inflated state. FIG. 8D depicts the intravaginal support apparatus 50 when it supports a balloon having a rounded oval shape in an inflated state. Different balloons may be sized and shaped to provide different support for different vaginal disorders and/or to fit different vaginal lumen volumes. For example, FIGS. 9A-9C depicts the intravaginal support apparatus 50 when it supports balloons having different exemplary shapes, for example FIG. 9A depicts a box shaped balloon, FIG. 9B depicts an oval shaped balloon, and FIG. 9C depicts a pyramid shaped balloon. Each one of the shapes may be selected to apply pressures in different patterns (e.g. location and pressure level) on the inner walls of the vagina. It should be emphasized that different combinations of balloons with different shapes and sizes may be provided, for example large pyramid anterior balloons with small box posterior balloons. Optionally, the balloons are sized and shaped to allow vaginal secretion flow in the vaginal lumen and/or out from the vaginal lumen. This flow is facilitated in the space between the folding of the balloon and/or in spaces formed as a result of the inflation of the balloon.

Optionally, the expandable elements, for example the balloons, which are mounted on the intravaginal support apparatus 50, are set to apply pressure, when inflated within the intravaginal lumen, on suture lines so as to prevent oozing and exposure to high intra abdominal pressure which may cause premature separation and/or inappropriate healing.

Optionally, the expandable elements, for example the balloons, which are mounted on the intravaginal support apparatus 50, are set to apply pressure so as to control bleeding, to provide Vaginal wall support and/or provide Vaginal packing.

Optionally, a plurality of balloons 421 are mounted on the carrier 451. In these embodiments, the inner conduit has a plurality of outlets, each connected to another balloon. Each one of the plurality of outlets may be connected to another balloon. Optionally, the diameter of the plurality of outlets is adapted to a desired inflation rate, facilitating the inflation of some balloons before others.

Optionally, the expandable elements are expanded to apply a selected pressure on the vaginal walls, for example by controlling an inflating fluid pressure. The inflating fluid pressure may be controlled according the reading of a pressure gauge which is connected to the external conduit 456 and/or placed within the balloon. Optionally, the selected pressure is applied according to a preprogrammed and/or a dynamic schema which is selected according to one or more characteristics of the patient and/or the required treatment, for example according to the patient age and/or medical condition and/or indication and/or treatment protocol. Optionally, the selected pressure is applied by using a pump which delivers and/or extracts fluids into or from the balloons 420/421. Optionally, the pump is controlled by a controller which operates according to a selected plan and/or according to readings of the pressure gauge.

Figure 10A:
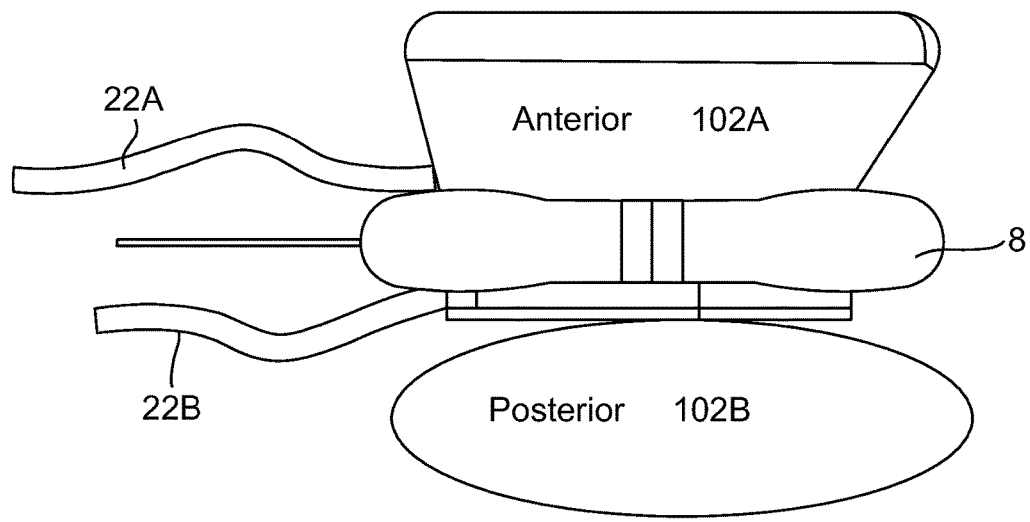
FIGS. 10A and 10B are schematic illustrations which depict a vaginal support apparatus having a carrier which is set to support a plurality of balloons from which at least two are placed in opposing sides of the intravaginal support apparatus 50, according to some embodiments of the present invention.
Figure 10B:
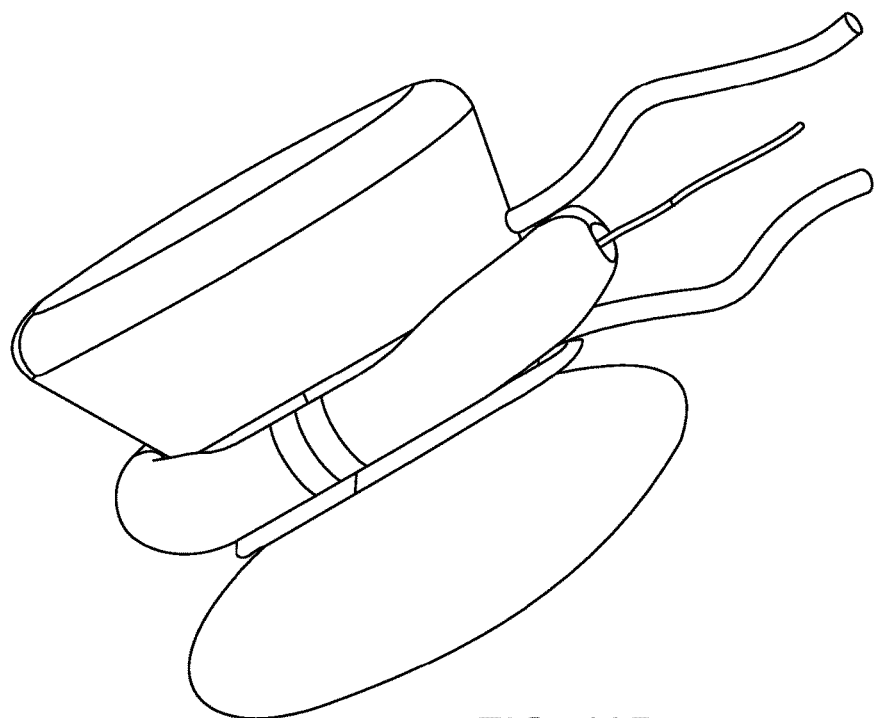

According to some embodiments of the present invention, for example as depicted in FIGS. 10A and 10B, the carrier 451 is set to support a plurality of balloons from which at least two are placed in opposing sides of the intravaginal support apparatus 50, for example above and below the intravaginal support apparatus 50, as shown at FIGS. 10A and 10B and/or to the left and right sides of the intravaginal support apparatus 50.

According to some embodiments of the present invention, the carrier 451 is set to support a U-shaped balloon 801 which covers portions of the top and bottom sides of the carrier 451, for example as shown at FIGS. 11A-11H. The U-shaped balloon 801 allows wrapping the top and bottom inner walls of the vagina and applying tension on suture lines and vaginal meshes, such as meshes which are implanted during vaginal prolapse surgeries and the like. The U-shaped balloon 801 may have a single chamber and/or divided to a number of chambers which are inflated sequentially and/or simultaneously. Optionally, the one or more chambers are connected to a certain external conduit, as shown at FIGS. 11A-11H. Optionally, each chamber is separately connected to a different external conduit, as shown at FIGS. 11E-11H. This allows inflating the U-shaped balloon 801 to have different tensions at various sites around the vagina. Note that different balloons may have different sizes and volumes. The thickness (width and/or length) of the U-shaped balloon may vary from few millimeters to about 4 centimeters. Various parts of the U-shaped balloon may have different sizes, for example the apical part 802 may be wider and/or taller than anterior part 800 and/or posterior part 804.

Optionally, each external conduit is connected to a syringe and/or another device for injecting fluids into the connected chamber. Optionally, each external conduit is connected to a pressure gauge for measuring the pressure inside the connected chamber. It should be noted that the elements, which are supported by the intravaginal support apparatus 50, may be left uninflated and/or inflated few hours and/or days after the implanting of the intravaginal support apparatus 50. Optionally, the tension of the expandable elements is changed while the intravaginal support apparatus 50 is in the vaginal lumen, providing a dynamic support to the vaginal walls. In such a manner, the support may be increased and/or decreased gradually. For example, the intravaginal support apparatus 50 is placed within the vagina for a period of at least 24 hours, for example 24, 48, 72, 144 and/or any intermediate or longer period. The pressure within the one or more balloons may be adjusted, for example increased and/or reduced intermittently.

According to some embodiments of the present invention, the intravaginal support apparatus 50 includes one or more urethral support elements which are set to apply pressure or sub-urethral support against a vaginal wall and/or the urethra, for example as described in International Patent Application Pub. No. WO2008/152628 filed on Jun. 11, 2008, which is incorporated herein by reference. When the intravaginal support apparatus 50 is implanted, the urethral support element serves as an external sphincter for the urethra to selectable controlled urination and thus continence. Optionally, a safety mechanism is provided to activate automatically and/or deactivate the sphincter effect, for example, to prevent involuntary leakage and/or prevent urine retention. Optionally or alternatively, the urethral support element has a "base" stiffness degree and that stiffness can be varied, wither up or down, depending on need and/or implementation. Optionally, the ring tends to revert back to the base degree. Optionally or alternatively, the stiffening of the urethral support element is cyclical, for example, under electronic control, for example, using a motor which periodically increases and/or decreases stiffness, for example, by mechanically actuating one of the stiffening mechanisms described herein. Such a motor is optionally outside the body. The term "urethral support element" as used in this application refers to an element in any shape which can provide additional support to the urethra. For example, a ring according to some embodiments of the invention can be biased inward towards the central axis (creating a plus sign shaped support ring) or can consist of substantially straight segments (creating a quadrilateral, hexagonal or octagonal shaped or other polygonally shaped ring or be undulating or have a dimension perpendicular to the ring plane, for example a hollow cylinder or cone. Different shaped rings are optionally utilized depending on the needs of the individual wearer.

According to some embodiments of the present invention, the intravaginal support apparatus 50 is a post operative device for providing post surgical vaginal support.

Following a vaginal surgery, many surgeons prefer to leave a gauze within the vaginal lumen in order to prevent oozing and to support vaginal stabilization. The gauze is taken out several hours after the surgery, hence suture lines are left exposed to forces from the abdominal cavity, for example forces which are applied when the patient coughs, gets out of bed and/or as an outcome of constipation. It should be noted that such forces on exposed suture lines may cause initial damage leading to suture breakdown. Optionally, the intravaginal support apparatus 50 is implanted after the gauze is extracted. The intravaginal support apparatus 50 is left in the vaginal lumen for a few days to counteract forces from the abdominal cavity. Such a device may be left by the surgeon by the end of surgery, or following removal of the packing gauze. In other cases, if a packing vaginal wall device is left after surgery within the vagina, it may be left within the vagina with balloon either inflated or deflated. This is an example in which a U-shaped support device may serve for more than one indication.

According to some embodiments of the present invention, the intravaginal support apparatus 50 is set to support an expandable element, such as a balloon, that is be mounted on top of the pessary ring 302. For example, reference is now made to FIGS. 12A-12C which depict the intravaginal support apparatus 50 of FIG. 1 having the radial edges of a round balloon 501 attached to the pessary ring 302. Optionally, an external conduit 504 is connected to an internal conduit 503 which is placed within and/or along the walls of the pessary ring 302 to conduct fluids into the balloon 501. The internal conduit 503 has one or more outlets which are directed to be connected to the balloon 501, for example perpendicular to the main longitudinal axis of the external conduit 504. This allows inflating the round balloon 501 from the periphery of the vaginal support device 50, allowing using balloons without a direct connection to the carrier 51. It should be noted that the round balloon is stretched according to the configurations of the pessary ring 503.

According to some embodiments of the present invention, the intravaginal support apparatus 50 is set to support an irrigation unit for irrigating active agents, such as disinfectants and medicaments and/or diagnostic agents. For example, the intravaginal support apparatus 50 may be set to support a post operational irrigation unit that applies a continuous and/or an intermediate flow of active agents, such as disinfectants to prevent post surgical vaginal infection. For example, the disinfectants may include Betadine or local antibiotics, with or without systemic antibiotics. Optionally, the active agents are delivered using the irrigation unit during a period of few hours or more. Additionally, or alternatively, the carrier 51 may be set to support a pre operational irrigation unit that applies a continuous and/or an intermediate flow of active agents, such as disinfectants and or antibiotics, to de-colonize the vagina prior to a surgery so as to reduce the number of pathogens by douching the vagina. Optionally, the irrigation unit is connected to one or more external conduits, such as the aforementioned external conduits, which allow flowing one or more active agents, optionally in a fluid, thereto. For example, reference is now made to FIGS. 13A-13B which depict the intravaginal support apparatus 50 of FIG.1 having an annular irrigation unit 701 mounted thereon, according to some embodiments of the present invention. The irrigation unit 701 includes a conduit that is connected channels which are linked to an external source of fluid. For example, FIGS. 13A-13B depicts an exemplary irrigation unit 701 with such an irrigation channel 702. FIG. 13A shows a vaginal support device encircled with an irrigation unit 701 that comprises external irrigation channel 703 with output apertures 704. The exemplary irrigation unit 701 includes an external conduit, tube 722, which supplies liquid for irrigation. FIG. 13B depicts an irrigation unit having one or more channels which are placed within the walls of the pessary ring 302. Fluid is irrigated through holes 703. It should be noted that the irrigation unit may have outlets directed to various directions and placed in various locations along the ring. In such a manner, any irrigation pattern may be achieved. For example, while some of the outlets may be directed to face the space above and/or below the intravaginal support apparatus 50, others may be directed to face the space there around or any portion thereof. Optionally, when the irrigation unit 701 is implanted and used a pad for the absorption of discharges from the vagina is used.

According to some embodiments of the present invention, the intravaginal support apparatus 50 is set to support a drug delivery unit and/or covered with one or more layers of active agents, for releasing active agents, continually and/or intermittently, in the intravaginal lumen. Optionally, the layers and/or the drug delivery unit are in touch with the inner wall of the vagina. This allows releasing drugs and substances from the drug delivery device and/or layers into the vaginal wall. For example, at least the lateral sides of the pessary walls of the pessary ring 302 are covered with one or more layers of active agents so that the when the pessary ring 302 is held in a substantially annular configuration, the layers in touch with the inner walls of the vagina. /for example, an active agent, such as an intravaginal hormone, for example an Estrogen may be used before and following surgery in order to heal pressure wounds, make the vaginal tissue more pliable for surgery and to facilitate suture line healing following surgery. Additionally or alternatively, one or more balloons which are mounted on the intravaginal support apparatus 50 are covered with one or more layer of active agents, such as antibiotics or disinfectants.

According to some embodiments of the present invention, the intravaginal support apparatus 50 is set to support one or more expandable elements, such as balloons, for gradually expanding the intravaginal lumen over a period of minutes, hours, and/or days. For example, such a gradual expansion may follow or be a part of a widespread pelvic surgery with vaginal extension, pelvic irradiation, a surgery for neo-vagina formation and/or sexual therapy. The intravaginal support apparatus 50 serves as an anchor within the vagina with one or more expandable devices having a variable volume, shape and/or relative location (in relation to the intravaginal support apparatus 50, being able to expand, simultaneously or the one after the other in various orders. For example a gradual expansion, continuously or intermittently, may allow maintaining the volume of the intravaginal lumen in a fixed size for a period of minutes, hours, and/or days.

When the intravaginal support apparatus 50 is mounted in the intra-vaginal lumen, the one or more expandable elements which are supported by it are expanded. The expanded one or more expandable elements, which are anchored in the intravaginal lumen by the intravaginal support apparatus 50, optionally for long periods of few hours, days and/or weeks, expand the intravaginal lumen, for example widen and/or elongate the intravaginal lumen, while maintaining its flexibility, Optionally, the increased and/or constant pressure that is applied by the one or more expandable elements on the inner walls may be used to treat sexual disorders which require slow widening and lengthening of the vagina, for example vaginal narrowing.

It should be noted that the intravaginal support apparatus 50 with the one or more expandable elements may be used as a vaginal expander for various purposes and treatments. A physician and/or a surgeon may use the intravaginal support apparatus 50 in order to maintain vaginal flexibility, diameter and/or width, for various treatments, sexual disorders, and/or pre and/or post operation procedures.

According to some embodiments of the present invention, the carrier 451 is set to support one or more drug delivery element for a moderate and/or controlled release of drugs. The drug delivery elements may include capsules, an element with a dissolving drug delivery membrane and/or any passive or active drug delivery device.

According to some embodiments of the present invention, the carrier 451 is set support a n insemination device for controlled sequential and/or intermittent insemination during a period of few hours and days. The insemination device is optionally a slow-release insemination device which is anchored in the vagina for a period of few hours and days and enables in vivo and real-time insemination and/or sperm improvement. The process extends the window of opportunity for ovum fertilization by slow release of sperm into the uterine cavity and optionally by preventing loss of sperm by blocking the cervical cavity. Optionally, the insemination device includes a reservoir which is connected to a pump controlled by a microcontroller. The microcontroller activates the pump to release sperm from the reservoir in preset or dynamic patterns, according to a scheduled program and/or in response to the reading of one or more sensors for detecting ovulation, such as temperature sensors, chemical sensors and the like.

According to some embodiments of the present invention, the carrier 451 is set to support one or more intra-vaginal irradiation sources. In such a manner, the intravaginal support apparatus 50 may be used to anchor the intra-vaginal irradiation source(s) in the intravaginal lumen.

According to some embodiments of the present invention, the carrier 451 is set to support a pressure tool having an extending projection which is directed to a certain direction in relation to the vertical plane of the intravaginal support apparatus 50. In use, the intravaginal support apparatus 50 is implanted, for example as described above, anchoring the pressure tool in the vaginal lumen. Then, the extending projection of the pressure tool is extended in a certain angle in relation to the vertical plane of the intravaginal support apparatus 50, for example in parallel to the vertical plane, diagonally to the vertical plane, and/or perpendicular to the vertical plane. The extending applies pressure on a certain point on the inner walls of the vagina. For example, the pressure tool includes a slender balloon which is inflated using an external conduit, for example as described above with reference to FIGS. 7-8. Optionally, a number of pressure tools are placed on top of the carrier 451, facilitating the appliance of different or similar pressures in different directions. In another embodiment, the pressure tool includes an extending shaft, such as a telescopic shaft, that may be extended by a guidewire. The tip of the extending projection may be covered with medicaments. Optionally, the length of the extended projection may be between few centimeters and 20 centimeters, for example 5, 6, and 8 centimeters.

It should be noted that the intravaginal support apparatus 50 may be used to anchor any intravaginal unit in the intravaginal lumen by adjusting the carries to be attached thereto. Such an intravaginal support apparatus 50 is as a temporary scaffold for various intravaginal units. The anchoring of any of the aforementioned units in the intravaginal lumen may last for one or more hours.

Figure 14:
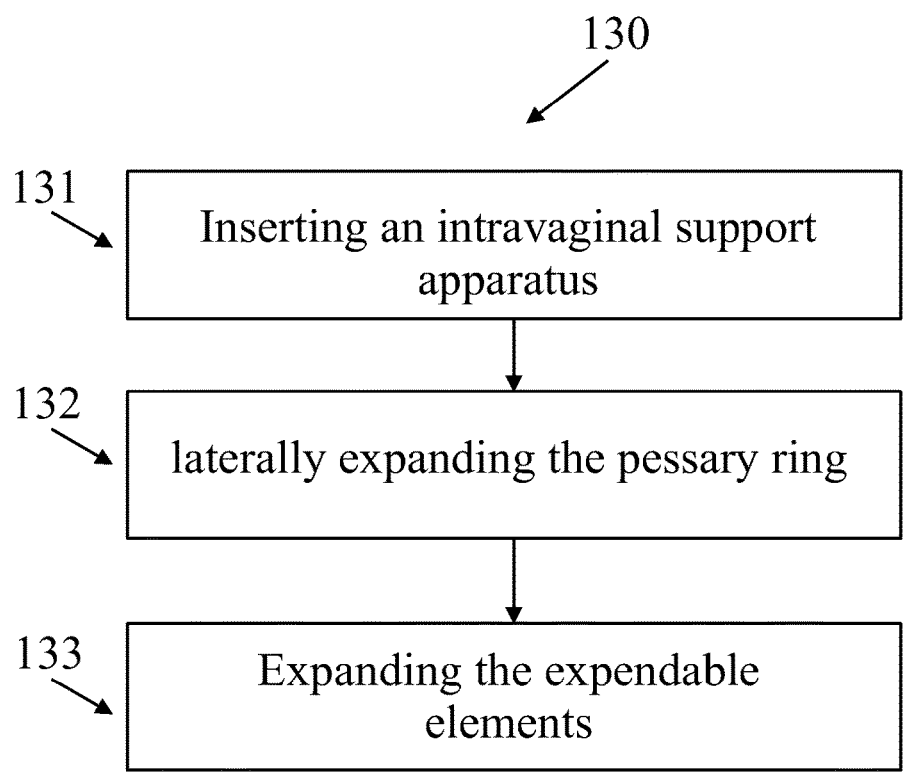
FIG. 14 is a flowchart of a method for providing intravaginal support using an intravaginal support apparatus, such as depicted in FIG. 1A, according to some embodiments of the present invention.

Reference is now made to FIG. 14, which is a flowchart of a method 130 for providing intravaginal support using an intravaginal support apparatus, such as one of the aforementioned intravaginal support apparatuses, according to some embodiments of the present invention. AS shown at 131, the method 130 is based on inserting the intravaginal support apparatus into an intravaginal lumen. Then, as shown at 132, the pessary ring is laterally expanded by inducing a switch between the narrowed configuration and the substantially annular configuration in the intravaginal lumen. This anchors the intravaginal support apparatus in a stationary location in the intravaginal lumen. Now, as shown at 133, the expandable elements expand at least downwardly and/or upwardly in the intravaginal lumen to provide intravaginal support, treatment and/or bleeding control.

It is expected that during the life of a patent maturing from this application many relevant methods and devices will be developed and the scope of the term an active agent, an expandable device and a balloon is intended to include all such new technologies a priori.

As used herein the term "about" refers to +/−10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An intravaginal support apparatus, comprising: a pessary ring having a substantially toroidal shape; wherein said pessary ring having a narrowed substantially oval-shaped configuration and a substantially annular configuration, and wherein a volume of said pessary ring in said narrowed substantially oval-shaped configuration is substantially equal to a volume of said pessary ring in said substantially annular configuration; a locking mechanism which retains and switches between said annular configuration and said narrowed oval-shaped configuration; wherein said locking mechanism is disposed in a region substantially inside a concentric hole formed by said pessary ring and is anchored to said pessary ring in two anchoring locations located on two opposing sides of a diameter of said pessary ring; and at least one expandable element having expanded and unexpanded configurations; a carrier mounted on said locking mechanism and having a width dimension set to fit within said region substantially inside said concentric hole formed by said pessary ring while in said narrowed oval-shaped configuration, said carrier maintains its position independently from said pessary ring when said pessary ring being switched between said annular configuration and said narrowed oval-shaped configuration; and a surface attached to said carrier by a connecting element selected from a group consisting of a flange, a clip and a fastener, said surface has a width dimension larger than a width of said pessary ring while in said narrowed oval-shaped configuration, said surface is adapted to attach said at least one expandable element thereabove; wherein said pessary ring is laterally expandable from said narrowed configuration to said annular configuration, said at least one expandable element is expandable outwardly of said pessary ring, from said unexpanded configuration to said expanded configuration.

2. The intravaginal support apparatus of claim 1, wherein said at least one expandable element expands at least one of upwardly of said pessary ring, in front of said pessary ring, forming an apical extension, and downwardly of said pessary ring.

3. The intravaginal support apparatus of claim 2, wherein said at least one expandable element is adapted to be switched from unexpanded configuration to expanded configurations by injecting fluids into said at least one expandable element.

4. The intravaginal support apparatus of claim 1, wherein said at least one expandable element comprises at least one balloon and at least one conduit for inflating said at least one balloon to switch between said unexpanded configuration and said expanded configuration.

5. The intravaginal support apparatus of claim 4, wherein said at least one balloon is attached to the surface of said pessary ring along an outer circumference, said at least one conduit being at least partly mounted within said pessary ring or along said outer circumference.

6. The intravaginal support apparatus of claim 4, wherein said at least one balloon comprises a plurality of balloons extending from opposing sides of said intravaginal support apparatus projecting along a circular axis of said pessary ring.

7. The intravaginal support apparatus of claim 4, further comprising a pressure gauge for measuring a pressure within said at least one balloon.

8. The intravaginal support apparatus of claim 4, further comprising a pump for delivering fluids into said at least one balloon according to said pump.

9. The intravaginal support apparatus of claim 4, further comprising a pump which is capable of delivering fluids into said at least one balloon and a controller which is capable of controlling said pump according to a selected pressure control plan.

10. The intravaginal support apparatus of claim 4, wherein said at least one balloon comprises a balloon having a shape selected from a group consisting of: an oval shape, a box shape, and a pyramid shape.

11. The intravaginal support apparatus of claim 1, wherein said at least one expandable element comprises a U-shaped balloon placed to expand projecting along a circular axis of said pessary ring outwardly above, projecting along the circular axis of said pessary ring outwardly below, and projecting perpendicularly to the circular axis of said pessary ring outwardly in front of said pessary ring.

12. The intravaginal support apparatus of claim 11, wherein U-shaped balloon having a plurality of compartments, each inflatable by applying a different pressure.

13. The intravaginal support apparatus of claim 1, wherein said at least one expandable element is attached on top of said pessary ring projecting along a circular axis of said pessary ring when in expanded configuration.

14. The intravaginal support apparatus of claim 1, wherein said at least one expandable element comprises a plurality of balloons and at least one conduit for inflating each said balloon in a different inflating rate.

15. The intravaginal support apparatus of claim 1, wherein said at least one expandable element comprises at least one of balloons, wire mesh structures and wire mesh structures covered with balloons.

16. The intravaginal support apparatus of claim 1, wherein said at least one expandable element comprises a U-shaped Balloon.

17. The intravaginal support apparatus of claim 1, wherein said at least one expandable element comprises a balloon divided to a number of chambers.

* * * * *